United States Patent
Williams et al.

(10) Patent No.: US 10,314,505 B2
(45) Date of Patent: Jun. 11, 2019

(54) ASYMMETRIC BASKET CATHETER

(71) Applicant: Biosense Webster (Israel) Ltd., Yokneam (IL)

(72) Inventors: Stuart Williams, Ontario, CA (US); Paul Tran, San Gabriel, CA (US); Mario A Solis, Rancho Cucamonga, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 393 days.

(21) Appl. No.: 15/070,213

(22) Filed: Mar. 15, 2016

(65) Prior Publication Data
US 2017/0265812 A1    Sep. 21, 2017

(51) Int. Cl.
| | | |
|---|---|---|
| *A61B 5/042* | (2006.01) | |
| *A61B 5/00* | (2006.01) | |
| *A61M 25/01* | (2006.01) | |
| *A61B 18/14* | (2006.01) | |
| *A61B 18/00* | (2006.01) | |
| *A61B 34/20* | (2016.01) | |

(52) U.S. Cl.
CPC .......... *A61B 5/0422* (2013.01); *A61B 5/6858* (2013.01); *A61B 18/1492* (2013.01); *A61M 25/0147* (2013.01); *A61B 2018/00196* (2013.01); *A61B 2018/00267* (2013.01); *A61B 2018/00351* (2013.01); *A61B 2018/00839* (2013.01); *A61B 2018/1467* (2013.01); *A61B 2034/2051* (2016.02)

(58) Field of Classification Search
CPC .................................................. A61B 5/0422
See application file for complete search history.

(56) References Cited

U.S. PATENT DOCUMENTS

| | | | |
|---|---|---|---|
| 5,391,199 A | | 2/1995 | Ben-Haim |
| 5,722,401 A | * | 3/1998 | Pietroski .............. A61B 5/0422 600/374 |
| 5,772,590 A | | 6/1998 | Webster, Jr. |
| 6,014,579 A | | 1/2000 | Pomeranz et al. |
| 6,064,905 A | | 5/2000 | Webster, Jr. |

(Continued)

FOREIGN PATENT DOCUMENTS

| | | |
|---|---|---|
| EP | 2752153 A1 | 7/2014 |
| WO | 96/05768 | 2/1996 |

(Continued)

OTHER PUBLICATIONS

U.S. Appl. No. 13/860,921, filed Apr. 11, 2013, entitled High Density Electrode Structure.

(Continued)

*Primary Examiner* — Lee S Cohen
(74) *Attorney, Agent, or Firm* — Dergosits & Noah LLP; Todd A. Noah

(57) ABSTRACT

This disclosure is directed to a catheter having an asymmetric basket-shaped electrode assembly at the distal end of the catheter body formed from a plurality of spines with electrodes. The plurality of spines are radially distributed across a first circumferential portion. One or more counter spines are radially distributed across a remaining second circumferential portion. Diagnostic electrodes are arrayed across the spines, while the counter spines may have one or more reference electrodes.

16 Claims, 4 Drawing Sheets

(56) References Cited

U.S. PATENT DOCUMENTS

| | | | |
|---|---|---|---|
| 6,216,043 B1* | 4/2001 | Swanson | A61B 5/0422 |
| | | | 600/374 |
| 6,239,724 B1 | 5/2001 | Doron et al. | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 6,748,255 B2 | 6/2004 | Fuimaono et al. | |
| 6,973,340 B2 | 12/2005 | Fuimaono et al. | |
| 7,377,906 B2 | 5/2008 | Selkee | |
| 8,137,308 B2 | 3/2012 | Schultz | |
| 8,346,339 B2* | 1/2013 | Kordis | A61B 5/0422 |
| | | | 600/374 |
| 9,204,929 B2* | 12/2015 | Solis | A61B 5/0422 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2012/0271135 A1* | 10/2012 | Burke | A61B 5/0422 |
| | | | 600/373 |
| 2015/0105645 A1 | 4/2015 | Subramaniam et al. | |
| 2015/0282859 A1* | 10/2015 | Bencini | A61B 18/02 |
| | | | 606/23 |
| 2017/0296084 A1* | 10/2017 | Blauer | A61B 5/6858 |

FOREIGN PATENT DOCUMENTS

| | | |
|---|---|---|
| WO | 98/18520 A2 | 5/1998 |
| WO | 11/014602 A1 | 2/2011 |

OTHER PUBLICATIONS

U.S. Appl. No. 14/063,477, filed Oct. 25, 2013, entitled Connection of Electrodes to Wires Coiled on a Core.

European Search Report for European Patent Application No. 17160862.3, dated Jul. 21, 2017; 9 pages.

* cited by examiner

ASYMMETRIC BASKET CATHETER

FIELD OF THE PRESENT DISCLOSURE

This invention relates to electrophysiologic (EP) catheters, in particular, EP catheters for mapping and/or ablation in the heart.

BACKGROUND

Electrophysiology catheters are commonly-used for mapping electrical activity in the heart. Various electrode designs are known for different purposes. In particular, catheters having basket-shaped electrode arrays are known and described, for example, in U.S. Pat. Nos. 5,772,590, 6,748,255 and 6,973,340, the entire disclosures of each of which are incorporated herein by reference, for use within a chamber of a patient's heart or similar region.

Basket catheters typically have an elongated catheter body and a basket-shaped electrode assembly mounted at the distal end of the catheter body. The basket assembly has proximal and distal ends and comprises a plurality of spines distributed around the circumference and connected at their proximal and distal ends. Each spine comprises at least one electrode, and typically several electrodes arrayed along the length of the spine. The basket assembly has an expanded arrangement wherein the spines bow radially outwardly and a collapsed arrangement wherein the spines are arranged generally along the axis of the catheter body. The collapsed arrangement facilitates introduction of the basket-shaped electrode assembly through the patient's vasculature while the expanded arrangement is intended to bring the electrodes arrayed along the spines into contact with the tissue defining the chamber in which the assembly is deployed.

It is desirable that a basket-shaped electrode assembly be capable of detecting as much information as possible as rapidly as possible. For example, it is desirable to capture, such as during a single beat, a wide picture of the electrical function of a region where the electrode assembly is deployed, such as the left or right atrium. As an illustration, fibrillation may present in a number of complex manners, including both paroxysmal as well as persistent atrial fibrillation and is not well understood. Attempts to characterize the conditions have employed a number of theories, including wavelet analysis, rotors and Shannon Entropy to identify the sources of perturbing electrical signals to facilitate quick and targeted ablation in such patients. As such, an expansive and accurate reflection of the electrical function in an affected region would confer considerable advantage when applying these and other techniques.

Conventional basket-shaped electrode assemblies are generally spherical and may be offered in a number of different sizes to help match the assembly to the particular anatomy of the patient. Nevertheless, such assemblies may not provide an optimal conformation to the anatomy of the chamber in which they are deployed. For example, some number of spines in a conventional basket-shaped electrode assembly may be in contact with openings in the chamber, such as the mitral valve. Accordingly, the signals collected from the electrodes on those spines do not contribute any meaningful information towards the analysis for finding the source of atrial fibrillation. The other spines, even if not positioned over an opening, may not be in optimal contact with the tissue defining the chamber, and suffer from degradation in the quality of information collected from their electrodes. Further, by seeking to come into contact with as much of the interior surface of the atrium or other chamber, convention basket-shaped electrode assemblies may be configured to assume a single, optimal shape that is generally spherical. Although different overall sizes may be provided, the inability to change the shape of the basket limits the ability of the assembly to have optimal contact with the atrial wall.

Accordingly, it would be desirable to provide a basket-shaped electrode assembly that distributes spines asymmetrically to allow the assembly to be positioned in an orientation that maximizes the number of spines in contact with a desired region of the chamber in which the assembly is deployed. It would also be desirable to prove a basket-shaped electrode assembly capable of assuming a variety of deployed, expanded arrangements to increase the number of electrodes that may be brought into contact with the chamber walls. The techniques of this disclosure as described in the following materials satisfy these and other needs.

SUMMARY

The present disclosure is directed to a catheter having an elongated catheter body with proximal and distal ends and at least one lumen therethrough and an asymmetric basket-shaped electrode assembly at the distal end of the catheter body, the asymmetric basket-shaped electrode assembly having a plurality of spines connected at their proximal and distal ends and radially distributed across a first circumferential portion, with each spine having a plurality of diagnostic electrodes, such that the asymmetric basket-shaped electrode assembly may have an expanded arrangement wherein the spines bow radially outwardly and a collapsed arrangement wherein the spines are arranged generally along a longitudinal axis of the catheter body.

In one aspect, the first circumferential portion may be non-spherical. For example, the first circumferential portion may be hemispheric.

In one aspect, the asymmetric basket-shaped electrode assembly may have at least one counter spine radially distributed across a remaining second circumferential portion. The at least one counter spine may have at least one reference electrode. In some embodiments, the asymmetric basket-shaped electrode assembly may have more spines than counter spines. In some embodiments, the number diagnostic electrodes per spine may be greater than the number of reference electrodes per counter spine.

In one aspect, a deployment member having proximal and distal ends may be slidably disposed within the lumen and aligned with the longitudinal axis of the catheter body, wherein the plurality of spines are attached at their distal ends to the deployment member, such that the asymmetric basket-shaped electrode assembly may have the collapsed arrangement when the deployment member is at a most distal position along the longitudinal axis relative to the catheter body. Proximal movement of the deployment member through a range of travel may be associated with conversion of the asymmetric basket-shaped electrode assembly to the expanded arrangement from the collapsed configuration. Relative movement of the deployment member through the range of travel may adjust the expanded arrangement by varying a length and a diameter of the asymmetric basket-shaped electrode assembly.

In one aspect, the asymmetric basket-shaped electrode assembly comprises an array having at least sixty diagnostic electrodes in the first circumferential portion and no diagnostic electrodes in the second circumferential portion.

In one aspect, the elongated catheter body is deflectable.

This disclosure also includes a method for mapping a chamber of a heart. The method may involve providing a catheter having an elongated catheter body with proximal and distal ends and at least one lumen therethrough and an asymmetric basket-shaped electrode assembly at the distal end of the catheter body, the asymmetric basket-shaped electrode assembly comprising a plurality of spines connected at their proximal and distal ends and radially distributed across a first circumferential portion, each spine comprising a plurality of diagnostic electrodes, and at least one counter spine radially distributed across a remaining second circumferential portion, introducing the distal end of the catheter into the chamber, expanding the asymmetric basket-shaped electrode assembly from a collapsed arrangement wherein the spines are arranged generally along a longitudinal axis of the catheter body, positioning the asymmetric basket-shaped electrode assembly within the chamber so that at least a portion of the diagnostic electrodes are in contact with tissue forming the chamber and recording electrical data received from the at least a portion of the diagnostic electrodes in contact with the tissue.

In one aspect, the chamber of the heart may be an atrium or a ventricle.

In one aspect, positioning the asymmetric basket-shaped electrode assembly within the chamber may involve orienting the asymmetric basket-shaped electrode assembly so that second circumferential portion is adjacent an area of reduced interest. For example, the area of reduced interest may be an opening of the chamber.

In one aspect, the catheter may also have a deployment member slidably disposed within the lumen and aligned with the longitudinal axis of the catheter body, wherein the plurality of spines are attached at their distal ends to the deployment member, so that the method may also involve adjusting a relative longitudinal position of the deployment member to vary a length and a diameter of the asymmetric basket-shaped electrode assembly to more closely conform to the chamber.

In one aspect, positioning the asymmetric basket-shaped electrode assembly within the chamber so that at least a portion of the diagnostic electrodes are in contact with tissue forming the chamber may involve deflecting the elongated catheter body.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

Figure 1:
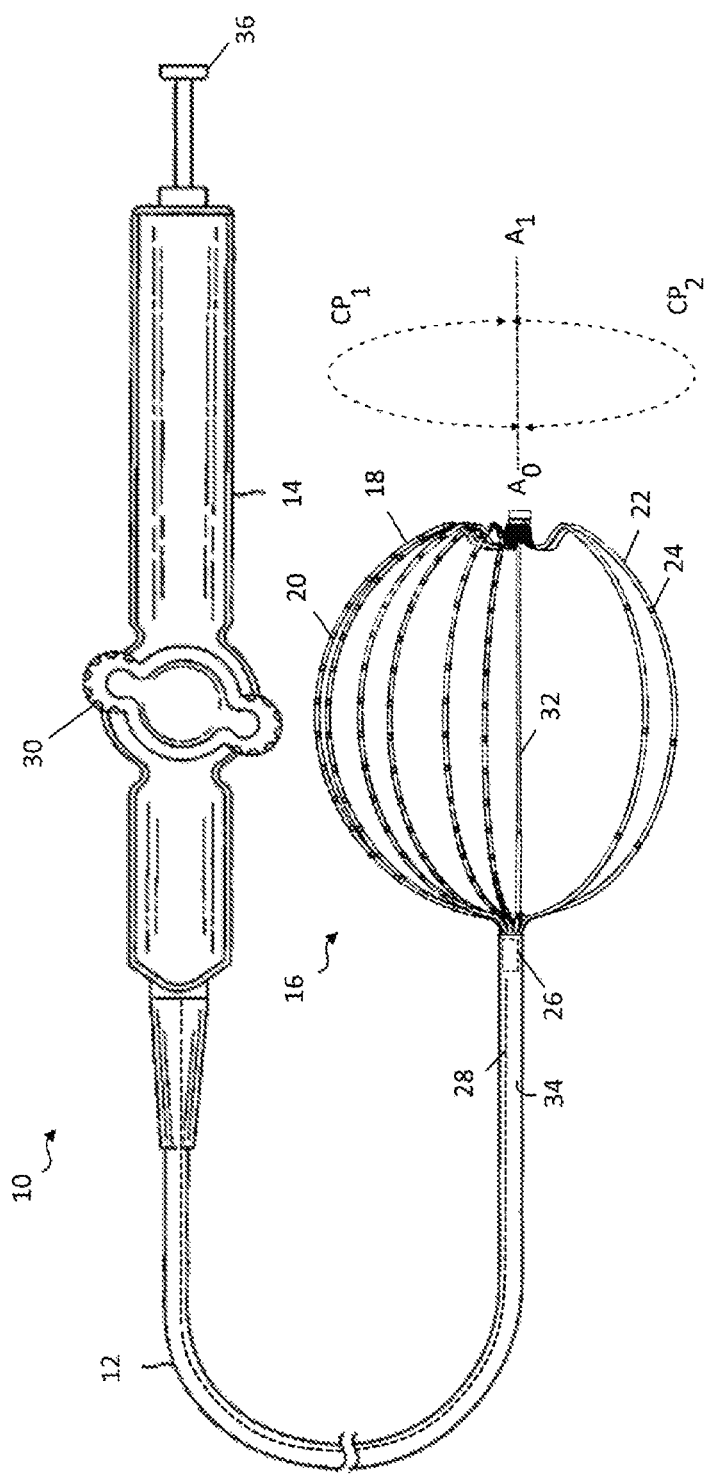
FIG. 1 is a top plan view of a catheter of the present invention, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Certain types of electrical activity within a heart chamber are not cyclical. Examples include arterial flutter or arterial fibrillation, and ventricular tachycardia originating in scars in the wall of the ventricle that have resulted from infarcts. Such electrical activity is random from beat to beat. To analyze or 'map' this type of electrical activity, it is desirable to obtain the 'picture' of a wide region as quickly as possible, such as within one heartbeat. In other words, all the points of the map or picture may be obtained simultaneously within one-tenth of a second. According to the techniques of this disclosure, an asymmetric basket-shaped electrode assembly may avoid areas of reduced interest, such as openings, to accurately map this electrical activity. Further, the disclosed asymmetric basket-shaped electrode assembly may be adjusted to have deployed arrangements with variable length and width to conform more closely to the anatomy of a given patient's heart. Still further, the catheter shaft may be deflectable to allow the operator to bring the asymmetric basket-shaped electrode assembly into increased contact with the walls of the chamber in which it is deployed.

To help illustrate aspects of this disclosure, one embodiment of an asymmetric basket-shaped electrode assembly is shown in FIG. 1, with catheter 10 comprises an elongated catheter body 12 having proximal and distal ends and a control handle 14 at the proximal end of the catheter body, with the asymmetric basket-shaped electrode assembly 16 mounted at the distal end of the catheter body 12. The asymmetric basket-shaped electrode assembly 16 has a plurality of spines 18, each carrying multiple diagnostic electrodes 20 for measuring electrical signals, radially distributed across a first, non-spherical circumferential portion $CP_1$ with respect to the longitudinal axis $A_0$-$A_1$ of catheter body 12, as schematically indicated. For example, the spines 18 may be arranged in a hemispherical configuration as shown in this embodiment, although designs occupying other proportions of the circumference may be employed. To enable accurate mapping of electrical signals, for example to detect a significant proportion of electrical function of the right or left atrium in as little as a single heartbeat, it may be desirable to provide an array of electrodes with a relatively high density. As such, the number of spines 18 employed in the first circumferential portion may be approximately three to six for a hemispheric portion, or any other suitable number for portions occupying other sized portions of the circumference. Spines 18 may be evenly or unevenly distributed radially within the first circumferential portion. Further, each spine 18 may include multiple electrodes 20, such as ten and up to approximately twenty electrodes per spine, or more. Similarly, the electrodes may be evenly distributed along the spine or may be skewed proximally, centrally or distally to facilitate analysis of the measured electrical signals.

As a first representative example, asymmetric basket-shaped electrode assembly 16 may have three spines 18, each with twenty diagnostic electrodes 20 to form an array of sixty electrodes. As will be appreciated, different numbers of spines 18 may be employed to provide a similar array, such as four spines having fifteen electrodes each, five spines having twelve electrodes each or six spines having ten electrodes. These examples are provided as illustrations only and without limitation, as other configurations of asymmetric basket-shaped electrode assembly 16 may utilize arrays having different numbers of electrodes, which may be implemented using any number of spines with any number of electrodes each. Further, as noted above asymmetric basket-shaped electrode assembly 16 may have a first circumferential portion occupied by spines 18 that is greater or less than the hemisphere depicted in FIG. 1. Accordingly, the number of spines 18 may be adjusted as appropriate. Depending on the number of spines and number of electrodes per spine, different techniques may be employed to accommodate the leads necessary to conduct the electrical signals to the proximal end of catheter 10 for recording. For example, each spine 18 may include cabling with built-in or embedded lead wires for the electrodes 20 carried by the spine as described in U.S. application Ser. No. 13/860,921, filed Apr. 11, 2013, entitled HIGH DENSITY ELECTRODE STRUCTURE, and U.S. application Ser. No. 14/063,477, filed Oct. 25, 2013, entitled CONNECTION OF ELECTRODES TO WIRES COILED ON A CORE, the entire disclosures of which are hereby incorporated by reference.

One or more counter spines 22 are radially distributed about the remaining second circumferential portion, indicated by $CP_2$. Any suitable number of counter spines 22 may be employed, so long as there are relatively fewer counter spines 22 than spines 18 in corresponding portions of the circumference. Optionally, one or more reference electrodes 24 may be present on one or more counter spines. Any number is suitable, but generally fewer reference electrodes 24 may be used per counter spine 22 as compared to the number of diagnostic electrodes 20 per spine 18. In some embodiments, reference electrodes 24 are not used for recording electrical signals or otherwise mapping electrical function. Reference electrodes 24 may be used in conjunction with a suitable location system, such as described in further detail below, to help determine the position and orientation of asymmetric basket-shaped electrode assembly 16 within the patient. Diagnostic electrodes 20 may also be used with the location system. Further, either or both spines 18 and counter spines 22 may have a pattern of radiopaque markers to help indicate orientation of asymmetric basket-shaped electrode assembly 16 under visualization. Additionally, one or more location sensors 26 may be provided near a distal end of the catheter 10 adjacent the asymmetric basket-shaped electrode assembly 16 as schematically indicated in FIG. 1. The sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils to enable a position determination (e.g., the location and orientation) of the distal end of catheter 10 within the heart cavity to be made.

In some embodiments, catheter shaft 12 may be deflectable to impart further control over which areas of tissue are contacted by asymmetric basket-shaped electrode assembly 16. At least one puller wire 28 may be secured at its distal end to a distal portion of catheter shaft 12 and at its proximal end to an actuator 30 on control handle 14. Rotating, or otherwise manipulating actuator 30 may place puller wire 28 under tension, producing a deflection of catheter shaft 12 away from its longitudinal axis. One puller wire may be employed to impart a uni-directional deflection, while an additional puller wire may provide bi-directional deflection. Examples of suitable construction details for deflectable catheters for are described in U.S. Pat. No. 7,377,906, entitled STEERING MECHANISM FOR BI-DIRECTIONAL CATHETER, and U.S. Pat. No. 8,137,308, entitled CATHETER WITH ADJUSTABLE DEFLECTION SENSITIVITY, the entire disclosures of which are hereby incorporated by reference. Other suitable techniques may also be employed to provide deflection as desired.

As noted, asymmetric basket-shaped electrode assembly 16 may also include a deployment member 32 disposed within a lumen 34 and generally coaxial with catheter body 12, extending from the proximal end of catheter body 12 and attached, directly or indirectly, to the distal ends of spines 18 and counter spines 22. The deployment member 32 may be coupled to an actuator 36 on control handle 14 and is afforded longitudinal movement relative to the catheter body so that it can move the distal ends of the spines 18 and counter spines 22 proximally or distally relative to the catheter body 12 to radially expand and contract, respectively, the electrode assembly. Since the proximal ends of spines 18 and counter spines 24 are secured to the catheter body 12, the distance between the distal and proximal ends of spines 18 and counter spines 24 shortens when they bow outwards into an expanded arrangement, which may be associated with relative movement of deployment member 32 in the proximal direction. In some embodiments, lumen 34 may also be used to supply a suitable irrigation fluid, such as heparinized saline, to the asymmetric basket-shaped electrode assembly 16. A fitting (not shown) in the control handle 14 may be provided to conduct irrigation fluid from a suitable source or pump into the lumen 26. Alternatively, the proximal portion of deployment member 32 may be tubular, such as in the form of a hypotube, which may feature a lumen used to deliver the irrigation fluid. In such embodiments, the irrigation fluid may be supplied through a fitting on actuator 34, for example.

Spines 18 and/or counter spines 22 may include a material as described below that facilitates assuming the expanded arrangement, such as a shape memory material, so that deployment member 32 may be omitted or may be used to aid the transition between the expanded and collapsed arrangements. In an embodiment, the deployment member 32 may comprise a wire or hypotube formed from a suitable shape memory material, such as a nickel titanium alloy as described below. As will be appreciated, different relative amounts of movement of the deployment member 32 along the longitudinal axis may affect the degree of bowing, such as to enable the spines 18 and counter spines 24 to assume different overall lengths and widths to more closely conform to the patient's anatomy and provide better contact between the tissue and electrodes 20 on spines 18. Thus, a user can modify the shape of the electrode assembly by adjusting the longitudinal extension or withdrawal of the puller.

Figure 2:
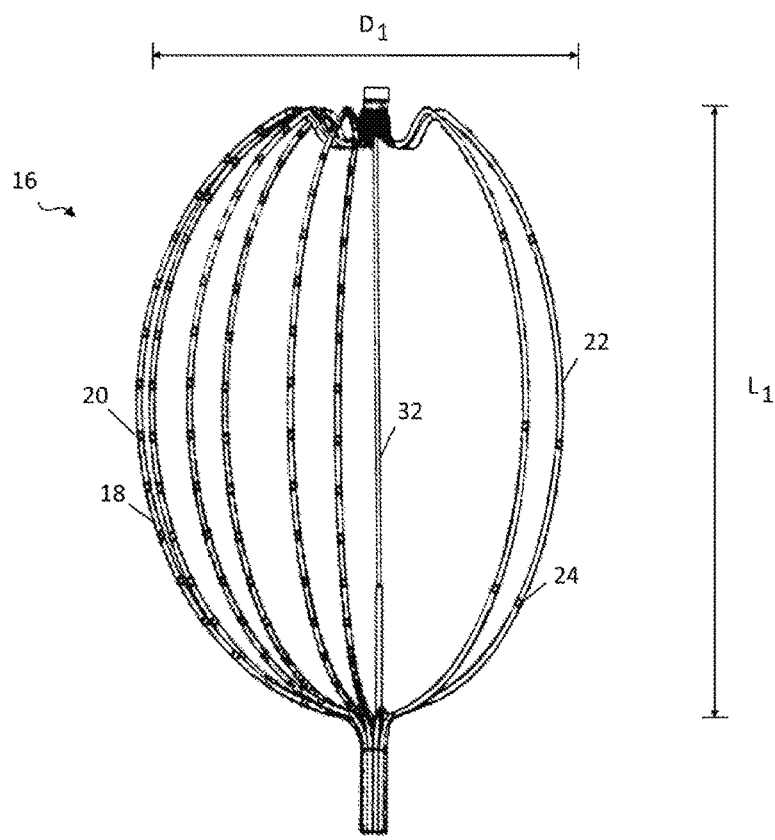
FIGS. 2 and 3 schematically show expanded arrangements of an asymmetric basket-shaped electrode assembly that depend on the relative longitudinal position of a deployment member, according to one embodiment.
Figure 3:
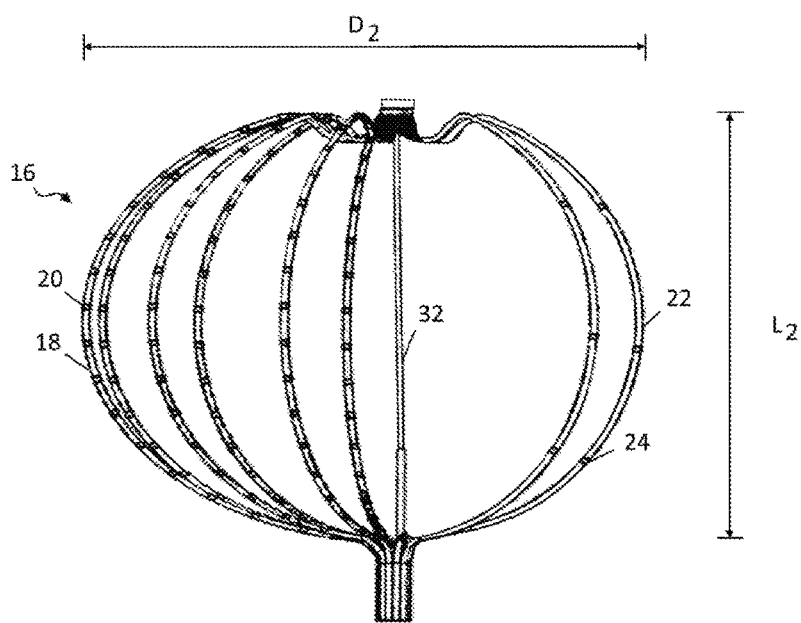

A range of travel of deployment member 32 from its most distal location to a relatively more proximal location corresponds to deflection of asymmetric basket-shaped electrode assembly 16 from a collapsed arrangement in which spines 18 and counter spines 24 are generally aligned with the longitudinal axis of catheter shaft 12 through varying dimensions having associated lengths and widths. Generally, as the distance between the proximal and distal ends of spines 18 and counter spines 22 is reduced, they bow outwards to a greater degree, increasing the effective diameter of asymmetric basket-shaped electrode assembly 16 as its length is reduced. For example, FIG. 2 schematically depicts a first arrangement of asymmetric basket-shaped electrode assembly 16 in which deployment member 32 has been withdrawn proximally a first amount. In this deployed arrangement, asymmetric basket-shaped electrode assembly 16 has a first length, $L_1$ as indicated, and a corresponding diameter, $D_1$. Correspondingly, FIG. 3 schematically depicts a second arrangement of asymmetric basket-shaped electrode assembly 16, in which deployment member 32 has been withdrawn proximally relative to the arrangement shown in FIG. 2, resulting in asymmetric basket-shaped electrode assembly 16 having a second length $L_2$ and second diameter $D_2$. As may be seen, $L_1$ is greater than $L_2$ which corresponds to diameter $D_1$ being less than diameter $D_2$. Deployment member 32 may be withdrawn any desired amount to provide an arrangement of spines 18 and counter spines 22 having a corresponding length and diameter to more closely conform to the patient's anatomy.

As noted, spines 18 and counter spines 22 may be generally aligned with the longitudinal axis of catheter body 12 in a collapsed arrangement to facilitate delivery, such as by reducing the outer diameter for insertion within and withdrawal from the patient. In some embodiments, the spines and counter spines may be constrained in the collapsed arrangement, such as by a guiding sheath. Further, spines 18 and/or counter spines 22 may include a sufficient resilient material so that they assume an expanded deployed configuration when unconstrained with relatively little or no force applied to deployment member 32. Alternatively, spines 18 and/or counter spines 22 may be configured to remain in the collapsed configuration even when unconstrained so that they may be deflected from the collapsed arrangement to a desired expanded arrangement by imparting sufficient force to deployment member 32.

The catheter body 12 comprises an elongated tubular construction having a single, axial or central lumen (not shown), but can optionally have multiple lumens if desired. The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 14 is rotated, the distal end of the catheter body will rotate in a corresponding manner. The outer diameter of the catheter body 12 is not critical, but generally should be as small as possible and may be no more than about 10 french depending on the desired application. Likewise, the thickness of the outer wall is not critical, but may be thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

Each spine 18 and counter spine 22 may comprise a flexible wire with a non-conductive covering on which one or more of the diagnostic electrodes 20 or reference electrodes 24 are mounted, such as in a ring electrode configuration. In an embodiment, the flexible wires may be formed from a shape memory material to facilitate the transition between expanded and collapsed arrangements and the non-conductive coverings may each comprise a biocompatible plastic tubing, such as polyurethane or polyimide tubing. In some embodiments, the flexible wire at the core of spines 18 and counter spines 22 may be formed as a framework cut from tubular stock. Alternatively, in some embodiments the spines 18 and/or counter spines 22 can be designed without the internal flexible wire if a sufficiently rigid and resilient polymeric material is used that permits radial expansion of the asymmetric basket-shaped electrode assembly 16, while providing a nonconductive outer surface for mounting of the electrodes.

In some embodiments, the framework or other configuration of flexible wires used for spines 18 and counter spines 22 may be formed from nickel-titanium alloys known as nitinol. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape" that is dependent on its temperature phases. The austenite phase is nitinol's stronger, higher-temperature phase, with a simple cubic crystalline structure. Superelastic behavior occurs in this phase (over a 50°-60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature. Accordingly, the asymmetric basket-shaped electrode assembly 16 may have a three dimensional shape that can be easily collapsed to be fed into a guiding sheath and then readily returned to its expanded shape memory configuration upon delivery to the desired region of the patient upon removal of the guiding sheath.

Figure 4:
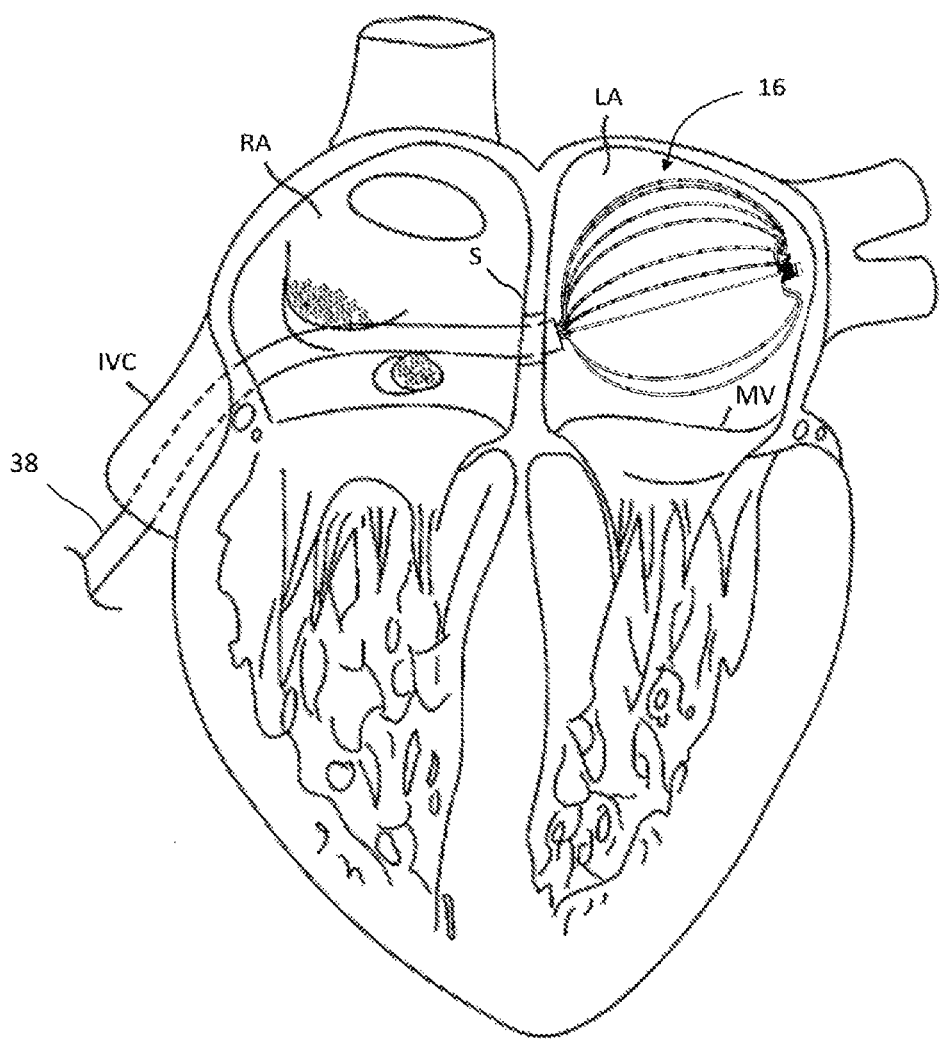
FIG. 4 is a schematic view of an asymmetric basket-shaped electrode assembly within the left atrium, according to one embodiment.

In one aspect, an electrophysiologist may introduce a guiding sheath, guidewire and dilator into the patient, as is generally known in the art. Examples of suitable guiding sheaths for use in connection with the inventive catheter are the PREFACE™ Braided Guiding Sheath (commercially available from Biosense Webster, Inc., Diamond Bar, Calif.) and the DiRex™ Guiding Sheath (commercially available from BARD, Murray Hill, N.J.). The guidewire is inserted, the dilator is removed, and the catheter is introduced through the guiding sheath whereby the guidewire lumen in the puller permits the catheter to pass over the guidewire. In one exemplary procedure as depicted in FIG. 4, the catheter is first introduced to the right atrium (RA) via the inferior vena cava (IVC), where it passes through the septum (S) in order to reach the left atrium (LA).

As will be appreciated, the guiding sheath 38 covers the spines 18 of the asymmetric basket-shaped electrode assembly 16 in a collapsed position so that the entire catheter can be passed through the patient's vasculature to the desired location. The deployment member 32 may be positioned distally of the catheter body to allow the spines of the assembly to be flattened while the assembly is passed through the guiding sheath. Once the distal end of the catheter reaches the desired location, e.g., the left atrium, the guiding sheath is withdrawn to expose the asymmetric basket-shaped electrode assembly 16. The deployment member 32 is drawn proximally through its first range of travel or otherwise manipulated so that the spines 18 and counter spines 22 flex outwardly between the distal and proximal junctions. With the asymmetric basket-shaped electrode assembly 16 radially expanded, the diagnostic electrodes 20 arrayed across the first circumferential portion contact atrial tissue. As recognized by one skilled in the art, the relative longitudinal position of deployment member 32 may be adjusted so that asymmetric basket-shaped electrode assembly 16 assumes a length and diameter that closely conforms to the area in which it is deployed as discussed above. Further, asymmetric basket-shaped electrode assembly 16 may be oriented so that the second circumferential portion is oriented towards an area that is not expected to provide meaningful information regarding electrical function, such as towards the mitral valve (MV), another opening or other area of reduced interest.

When the asymmetric basket-shaped electrode assembly 16 is expanded into an expanded arrangement, the electrophysiologist may map local activation time and/or ablate using diagnostic electrodes 20, which can guide the electrophysiologist in diagnosing and providing therapy to the patient. As noted, the catheter may include one or more reference ring electrodes 24 mounted on counter spines 22, or other reference electrodes on the catheter body and/or one or more reference electrodes may be placed outside the body of the patient. By using the inventive catheter with the multiple electrodes on the basket-shaped electrode assembly, the electrophysiologist can obtain a true anatomy of a cavernous region of the heart, including an atrium, by avoiding areas unlikely to have useful electrical information and by more closely conforming to the patient's anatomy, allowing a more rapid mapping of the region.

Figure 5:
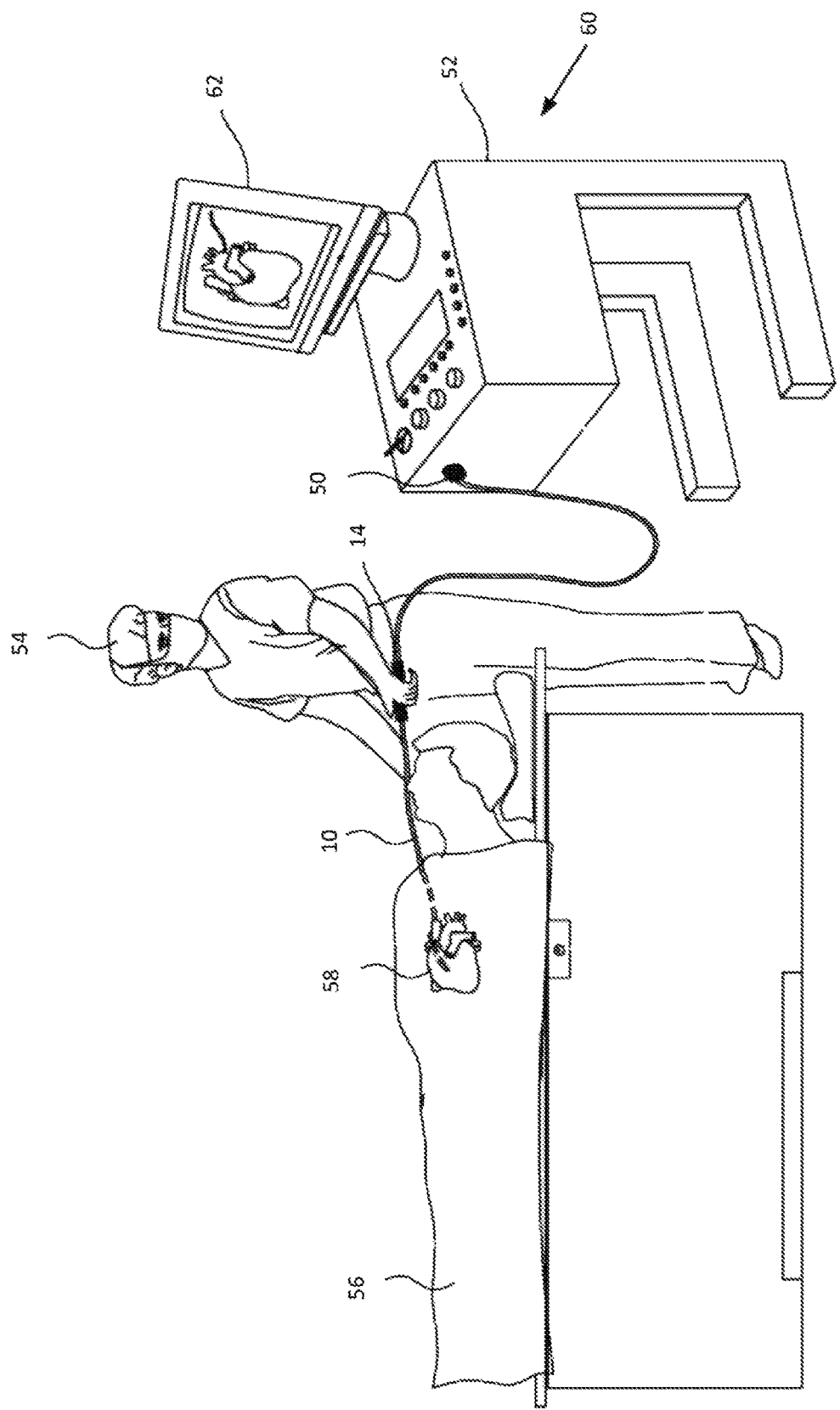
FIG. 5 is a schematic illustration of an invasive medical procedure using an asymmetric basket-shaped electrode assembly, according to one embodiment.

To help illustrate use of the asymmetric basket-shaped electrode assembly 16, FIG. 5 is a schematic depiction of an invasive medical procedure, according to an embodiment of the present invention. Catheter 10, with the basket-shaped electrode assembly 16 (not shown in this view) at the distal end may have a connector 50 at the proximal end for coupling the wires from their respective diagnostic electrodes 20 (not shown in this view) to a console 52 for recording and analyzing the signals they detect, as well as coupling to reference electrodes 24 for location determination. An electrophysiologist 54 may insert the catheter 10 into a patient 56 in order to acquire electropotential signals from the heart 58 of the patient. The professional uses the control handle 14 attached to the catheter in order to perform the insertion. Console 52 may include a processing unit 60 which analyzes the received signals, and which may present results of the analysis on a display 62 attached to the console. The results are typically in the form of a map, numerical displays, and/or graphs derived from the signals.

In a further aspect, the processing unit 60 may also receive signals from one or more location sensors 26 provided near a distal end of the catheter 10 adjacent the asymmetric basket-shaped electrode assembly 16 and/or reference electrodes 24. The sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 60 to determine the position, (e.g., the location and orientation) of the distal end of catheter 10 within the heart cavity. The electrophysiologist may then view the position of the asymmetric basket-shaped electrode assembly 16 on an image the patient's heart on the display 62. By way of example, this method of position sensing may be implemented using the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally with respect to electrode array assembly 16. The coordinates of the distal sensor relative to the proximal sensor may be determined and, with other known information pertaining to the configuration of asymmetric basket-shaped electrode assembly 16, including reference electrodes 24, used to find the positions of each of the diagnostic electrodes 20.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising an elongated catheter body having proximal and distal ends and at least one lumen therethrough and an asymmetric basket-shaped electrode assembly at the distal end of the catheter body, the asymmetric basket-shaped electrode assembly comprising a plurality of spines connected at their proximal and distal ends and radially distributed across a first circumferential portion, each spine comprising a plurality of diagnostic electrodes, and comprising at least one counter spine radially distributed across a remaining second circumferential portion, at least one counter spine comprising at least one reference electrode, wherein the asymmetric basket-shaped electrode assembly has an expanded arrangement wherein the spines bow radially outwardly and a collapsed arrangement wherein the spines are arranged generally along a longitudinal axis of the catheter body.

2. The catheter of claim 1, wherein the first circumferential portion is non-spherical.

3. The catheter of claim 2, wherein the first circumferential portion is hemispheric.

4. The catheter of claim 1, wherein the asymmetric basket-shaped electrode assembly has more spines than counter spines.

5. The catheter of claim 1, wherein each spine has a number diagnostic electrodes per spine and wherein each counter spine has a number of reference electrodes per counter spine, such that the number diagnostic electrodes per spine is greater than the number of reference electrodes per counter spine.

6. The catheter of claim 1, further comprising a deployment member having proximal and distal ends, the deployment member slidably disposed within the lumen and aligned with the longitudinal axis of the catheter body, wherein the plurality of spines are attached at their distal ends to the deployment member, such that the asymmetric basket-shaped electrode assembly has the collapsed arrangement when the deployment member is at a most distal position along the longitudinal axis relative to the catheter body.

7. The catheter of claim 6, wherein proximal movement of the deployment member through a range of travel is associated with conversion of the asymmetric basket-shaped electrode assembly to the expanded arrangement from the collapsed configuration.

8. The catheter of claim 7, wherein relative movement of the deployment member through the range of travel adjusts the expanded arrangement by varying a length and a diameter of the asymmetric basket-shaped electrode assembly.

9. The catheter of claim 1, wherein the asymmetric basket-shaped electrode assembly comprises an array having at least sixty diagnostic electrodes in the first circumferential portion and no diagnostic electrodes in the second circumferential portion.

10. The catheter of claim 1, wherein the elongated catheter body is deflectable.

11. A method for mapping a chamber of a heart comprising:

providing a catheter having an elongated catheter body with proximal and distal ends and at least one lumen therethrough and an asymmetric basket-shaped electrode assembly at the distal end of the catheter body, the asymmetric basket-shaped electrode assembly comprising a plurality of spines connected at their proximal and distal ends and radially distributed across a first circumferential portion, each spine comprising a plurality of diagnostic electrodes, and at least one counter spine radially distributed across a remaining second circumferential portion, the at least one counter spine comprising at least one reference electrode;

introducing the distal end of the catheter into the chamber;

expanding the asymmetric basket-shaped electrode assembly from a collapsed arrangement wherein the spines are arranged generally along a longitudinal axis of the catheter body;

positioning the asymmetric basket-shaped electrode assembly within the chamber so that at least a portion of the diagnostic electrodes are in contact with tissue forming the chamber; and recording electrical data received from the at least a portion of the diagnostic electrodes in contact with the tissue.

12. The method of claim 11, wherein the chamber of the heart is an atrium or a ventricle.

13. The method of claim 11, wherein positioning the asymmetric basket-shaped electrode assembly within the chamber comprises orienting the asymmetric basket-shaped electrode assembly so that second circumferential portion is adjacent an area of reduced interest.

14. The method of claim 13, wherein the area of reduced interest is an opening of the chamber.

15. The method of claim 11, wherein the catheter further comprises a deployment member having proximal and distal ends, the deployment member slidably disposed within the lumen and aligned with the longitudinal axis of the catheter body, wherein the plurality of spines are attached at their distal ends to the deployment member, further comprising adjusting a relative longitudinal position of the deployment member to vary a length and a diameter of the asymmetric basket-shaped electrode assembly to more closely conform to the chamber.

16. The method of claim 11, wherein positioning the asymmetric basket-shaped electrode assembly within the chamber so that at least a portion of the diagnostic electrodes are in contact with tissue forming the chamber comprises deflecting the elongated catheter body.

\* \* \* \* \*